US012291744B2

(12) United States Patent
Nelson

(10) Patent No.: US 12,291,744 B2
(45) Date of Patent: *May 6, 2025

(54) METHODS FOR ENRICHING A TARGET POLYNUCLEOTIDE IN A SAMPLE

(71) Applicant: NEXGEN CANCER DETECTION LLC, Lino Lakes, MN (US)

(72) Inventor: Matthew Nelson, Lino Lakes, MN (US)

(73) Assignee: NEXGEN CANCER DETECTION LLC, Lino Lakes, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/821,044

(22) Filed: Aug. 30, 2024

(65) Prior Publication Data

US 2025/0011855 A1 Jan. 9, 2025

Related U.S. Application Data

(63) Continuation of application No. 18/691,325, filed as application No. PCT/US2022/043169 on Sep. 11, 2022.

(60) Provisional application No. 63/243,390, filed on Sep. 13, 2021.

(51) Int. Cl.
*C12Q 1/6858* (2018.01)
*C12Q 1/6886* (2018.01)

(52) U.S. Cl.
CPC ......... *C12Q 1/6858* (2013.01); *C12Q 1/6886* (2013.01); *C12Q 2537/163* (2013.01); *C12Q 2600/156* (2013.01)

(58) Field of Classification Search
None
See application file for complete search history.

(56) References Cited

U.S. PATENT DOCUMENTS

| 9,957,556 | B2 | 5/2018 | Makrigiorgos | |
| 2011/0217714 | A1* | 9/2011 | Makrigiorgos | ...... C12Q 1/6858 435/6.12 |
| 2019/0085400 | A1 | 3/2019 | Christensen | |

FOREIGN PATENT DOCUMENTS

WO WO2021050100 A1 * 3/2021

OTHER PUBLICATIONS

Cline et al. Nucleic Acids Research. 24(18): 3546-3551 (Year: 1996).*
Huang et al Molecular and Cellular Probes. 2010. 24: 376-380) (Year: 2010).*
Albitar et al J visualized Experiments. 121: e55130, 8 pages (Year: 2017).*
Mauger et al. Mol Diagn Ther. 21: 269-283 (Year: 2017).*
Agilent, "High-Fidelity PCR Enzymes: Properties and Error Rate Determinations", https://www.agilent.com/cs/librarytechnicaloverviews/public/technical%20note_high-fidelity%20PCR%20enzymes_5994-0929en_.pdf, 13 pages (2019).
Braasch, D, et al., "Locked nucleic acid (LNA): fine-tuning the recognition of DNA and RNA", Chemistry & Biology 8 (1), 1-7 (2001).
Dominguez, P, et al., "Wild-type blocking polymerase chain reaction for detection of single nucleotide minority mutations from clinical specimens", Oncogene 24 (45), 6830-6834 (2005).
Gilje, B, et al., "High-Fidelity DNA Polymerase Enhances the Sensitivity of a Peptide Nucleic Acid Clamp PCR Assay for K-ras Mutations", J Mol Diagn 10 (4), 325-331 (2008).
Lv, X, et al., "Detection of Rare Mutations in CtDNA Using Next Generation Sequencing", J Vis Exp 126, e56342, 8 pages (2017).
Menchise, V, et al., "Insights into peptide nucleic acid (PNA) structural features: The crystal structure of a d-lysine-based chiral PNA-DNA duplex", Proc Natl Acad Sci 100 (21), 12021-12026 (2003).
Milbury, C, et al., "Ice-COLD-PCR enables rapid amplification and robust enrichment for low-abundance unknown DNA mutations", Nucleic Acids Res 39 (1), e2, 1-10 (2011).
Patent Cooperation Treaty, International Search Report and Written Opinion for PCT/US2022/043169, 9 pages, dated May 1, 2023.
Potaman, V, et al., "DNA: Alternative Conformations and Biology", Madame Curie Bioscience Database [Internet], Landes Bioscience 2000-2013, 17 pages (2013).
Smolina, I, et al., "Detection of Low-Copy-Number Genomic DNA Sequences in Individual Bacterial Cells by Using Peptide Nucleic Acid-Assisted Rolling-Circle Amplification and Fluorescence In Situ Hybridization", Applied and Environmental Microbiology 73 (7), 2324-2328 (2007).
Sun, Q, et al., "A novel xenonucleic acid-mediated molecular clamping technology for early colorectal cancer screening", PLoS One 16 (10), e0244332, 1-16 (2021).
Thiede, C, et al., "Simple and sensitive detection of mutations in the ras proto-oncogenes using PNA-mediated PCR clamping", Nucleic Acids Res 24 (5), 983-984 (1996).
Vliegen, L, et al., "Validation of a locked nucleic acid based wild-type blocking PCR for the detection of EGFR exon 18/19 mutations", Diagn Pathol 10, 57, 1-8 (2015).
Zhang, T, et al., "Novel XNA Molecular Clamp Application in NGS Diagnostic Platform OptiSeq TM Cancer Panels", Bio-IT World Conference & Expo, San Francisco, California, 1 page (Mar. 1, 2020).

(Continued)

*Primary Examiner* — Carla J Myers
(74) *Attorney, Agent, or Firm* — Viksnins Harris Padys Malen LLP

(57) ABSTRACT

Disclosed are methods for detecting a target polynucleotide comprising a genetic alteration relative to a reference polynucleotide in a sample comprising a mixture of the target polynucleotide and the reference polynucleotide. The methods may be utilized for detecting with high selectivity a target polynucleotide in a mixture of the reference polynucleotide and the target polynucleotide in which the target polynucleotide represents a low percentage of the mixture. The methods may be adapted for diagnosing, prognosing, and treating subjects having a disease or disorder associated with the genetic alteration.

7 Claims, 2 Drawing Sheets

Specification includes a Sequence Listing.

(56) References Cited

OTHER PUBLICATIONS

Cofsky, J, et al., "Crystal structure of an RNA/DNA strand exchange junction", PLoS One 17 (4), e0263547, 15 pages (2022).
Hardison, R , "Working With Molecular Genetics", The Pennsylvania State University Book: Working with Molecular Genetics 6 pages (2024).
Pande, V, et al., "Insights into structure, dynamics and hydration of locked nucleic acid (LNA) strand-based duplexes from molecular dynamics simulations", Nucleic Acids Research 36 (5), 1508-1516 (2008).

* cited by examiner

SEQUENCE LISTING

```
Sequence total quantity: 5
SEQ ID NO: 1            moltype = DNA   length = 143
FEATURE                 Location/Qualifiers
source                  1..143
                        mol_type = genomic DNA
                        organism = Homo sapiens
SEQUENCE: 1
cttatgtgtg acatgttcta atatagtcac attttcatta tttttattat aaggcctgct   60
gaaaatgact gaatataaac ttgtggtagt tggagctggt ggcgtaggca agagtgcctt   120
gacgatacag ctaattcaga atc                                          143

SEQ ID NO: 2            moltype = DNA   length = 143
FEATURE                 Location/Qualifiers
source                  1..143
                        mol_type = genomic DNA
                        organism = Homo sapiens
variation               98
SEQUENCE: 2
cttatgtgtg acatgttcta atatagtcac attttcatta tttttattat aaggcctgct   60
gaaaatgact gaatataaac ttgtggtagt tggagcttgt ggcgtaggca agagtgcctt   120
gacgatacag ctaattcaga atc                                          143

SEQ ID NO: 3            moltype = DNA   length = 18
FEATURE                 Location/Qualifiers
source                  1..18
                        mol_type = other DNA
                        organism = synthetic construct
SEQUENCE: 3
cttatgtgtg acatgttc                                                18

SEQ ID NO: 4            moltype = DNA   length = 20
FEATURE                 Location/Qualifiers
source                  1..20
                        mol_type = other DNA
                        organism = synthetic construct
SEQUENCE: 4
gattctgaat tagctgtatc                                              20

SEQ ID NO: 5            moltype = DNA   length = 10
FEATURE                 Location/Qualifiers
source                  1..10
                        mol_type = other DNA
                        organism = synthetic construct
modified_base           1..10
                        mod_base = OTHER
                        note = Locked Nucleic Acids
SEQUENCE: 5
agctggtggc                                                         10
```

METHODS FOR ENRICHING A TARGET POLYNUCLEOTIDE IN A SAMPLE

CROSS-REFERENCE TO RELATED APPLICATIONS

This application is a continuation of U.S. patent application Ser. No. 18/691,325, filed Mar. 12, 2024, which is a continuation of International Application Serial Number PCT/US2022/043169, filed Sep. 11, 2022, and claims the benefit of U.S. Provisional Application Ser. No. 63/243,390, filed Sep. 13, 2021. The entire content of the applications referenced above are hereby incorporated by reference herein.

SEQUENCE LISTING

The instant application contains a Sequence Listing which has been submitted in XML format via Patent Center and is hereby incorporated by reference in its entirety. Said XML copy, created on Sep. 13, 2022, is named 17038_001WO1_SL and is 27000 Bytes in size.

FIELD

The field of the invention relates to methods for detecting a target polynucleotide in a sample comprising a mixture of the target polynucleotide and a non-target polynucleotide. In particular, the field of the invention relates to methods for detecting a target polynucleotide that comprises a genetic alteration relative to a reference polynucleotide in a sample comprising a mixture of the target polynucleotide and the reference polynucleotide, where the target polynucleotide represents a relatively small percentage of the mixture. The methods may be adapted for diagnosing, prognosing, and treating subjects having a disease or disorder associated with the genetic alteration.

BACKGROUND

Genetic mutations and epigenetic modifications are known to be associated with cancer and other diseases. The ability to detect genetic mutations epigenetic modifications in cell-free DNA using a minimally invasive sample can be used in many different diagnostic areas, such as companion diagnostics, monitoring minimum residual disease, monitoring cancer recurrence, or as a prospective aid in diagnosing cancer.

In particular, early diagnosis of cancer, cancer recurrence or treatment resistant mutations can improve patient outcomes. Low sensitivity is important for early diagnosis, because mutant DNA represents a small percentage of DNA in biological sample relatively to wild-type DNA. High specificity is also important because of the negative impacts on patient health when a patient undergoes unnecessary cancer treatment, such as chemotherapy based on a false positive diagnosis.

One challenge to genetic diagnostics remains accurately determining the presence or absence of a mutation, when the mutant DNA can be present at very low concentrations compared to the wild-type DNA in a sample comprising a mixture of the mutant DNA and wild-type DNA. There have been many methods developed to detect a low-frequency mutation, such as digital droplet PCR, RT-PCR with modified oligonucleotides, BEAMing, Deep Sequencing, next-generation sequencing (NGS), and others. Although these methods have been shown to have very low sensitivity, one short-coming of these methods is that they may not achieve low specificity in combination with high sensitivity. In particular, next-generation sequencing (NGS) alone cannot accurately determine the presence or absence of a low-percentage variant having a single base mutation, partially because the error rate for NGS is too high. Despite all of the attempts to accurately determine the presence of a mutant DNA in an abundance of wild-type DNA, there is still a need for a better method.

Accuracy encompasses both specificity to reduce false-positives and sensitivity to reduce false-negatives. A threshold is used to define the barrier between a negative sample in which a mutation is absent and a positive sample where a mutation is present. This threshold is used to calculate the specificity and sensitivity of the method being used to detect the mutation. Similarly, the signal to noise ratio can be used to assess the accuracy of a method, where the signal represents the result when the mutation is present, and the noise represents the result when a mutation is absent. A method is more accurate as the separation between the signal and the noise becomes greater.

One approach to increasing the signal to noise ratio is to enrich the sample for the mutant. Enrichment may involve preferentially inhibiting or preventing the replication of wild type DNA relative to mutant DNA during PCR. In such enrichment, each cycle of PCR results in the mutant being present at a higher percentage compared to the previous cycle. However, no enrichment methods to date have been able to achieve adequate sensitivity and specificity.

As such, there remains a need for an accurate detection of a mutant DNA segment when the mutant DNA segment is present at a low percentage. This would benefit patients, particular regarding cancer diagnosis, by using liquid biopsy to determine the presence or absence of certain mutations associated with cancer. This could be applied to the various cancer diagnostic areas, such as companion diagnostics, minimum residual disease, cancer recurrence, or prospective aid in diagnosing cancer.

SUMMARY

The present inventor has discovered a method for detecting a target polynucleotide a target polynucleotide in a sample comprising a mixture of the target polynucleotide and a non-target polynucleotide, where the target polynucleotide represents a relatively small percentage of the mixture. The inventor's method can be utilized to selectively enrich a target polynucleotide via amplification relative to the non-target polynucleotide, and to accurately detect the target polynucleotide via sequencing when the target polynucleotide is present at a copy number lower than 10 and when the target polynucleotide represents less than about 0.125% of the mixture comprising the target polynucleotide and the non-target polynucleotide. In some embodiments, the inventor's method achieves an enrichment in which the target polynucleotide represents greater than about 99% of the sequenced amplification product (i.e., greater than about 99% of sequencing reads), representing a >700-fold enrichment, after the sample has been subjected to the inventor's amplification method and sequenced.

In some embodiments, the disclosed methods may be performed for detecting a target polynucleotide comprising a genetic alteration relative to a reference polynucleotide in a sample comprising a mixture of the target polynucleotide and the reference polynucleotide, where the reference polynucleotide is a non-target polynucleotide in the disclosed methods. The methods may be utilized for detecting with high sensitivity and high selectivity a target polynucleotide in a mixture of the target polynucleotide and the reference polynucleotide in which the target polynucleotide is present at a relatively low concentration in the sample (e.g., less than about 10 copies) and the target polynucleotide represents a low percentage of the mixture comprising the target polynucleotide and the reference polynucleotide (e.g., less than about 0.125% of the mixture). The methods may be adapted for diagnosing, prognosing, and treating subjects having a disease or disorder associated with the detected genetic alteration.

The disclosed methods typically include performing a polymerase chain reaction (PCR) amplification product which is subsequently sequenced in order to detect the target polynucleotide. The PCR reaction typically includes: (i) the sample or a fraction of the sample; (ii) a thermostable DNA polymerase that lacks 5'→3' nuclease activity and comprises 3'→5' nuclease activity (i.e., 3'→5' proofreading activity) and preferably has an error rate that is less than about $10^{-6}$ (i.e., a high fidelity DNA polymerase); (iii) a pair of primers that flank the genetic alteration to be detected in the method; and (iv) a blocking oligonucleotide that hybridizes selectively to the reference polynucleotide lacking the genetic alteration to form a blocking duplex (where the reference polynucleotide is a non-target polynucleotide), thereby selective blocking amplification of the reference polynucleotide and enriching amplification of the target polynucleotide. After amplification has been performed, the amplification product thereby obtained may be subjected to sequencing in order to detect the target polynucleotide. The disclosed methods achieve a remarkable level of enrichment where the target polynucleotide may represent greater than 99% of sequenced amplification product (i.e., greater than about 99% of sequencing reads), representing a >700-fold enrichment.

Also disclosed herein are kits for performing the disclosed methods. The disclosed kits may comprise one or more components for performing the disclosed methods selected from: (i) a thermostable DNA polymerase that lacks 5'→3' nuclease activity and comprises 3'→3' nuclease activity (i.e., 3'→5' proofreading activity) and preferably has an error rate that is less than about $10^{-6}$ (i.e., a high fidelity DNA polymerase); (iii) a pair of primers that flank a genetic alteration to be detected in the methods; and (iv) a blocking oligonucleotide that hybridizes selectively to the reference polynucleotide lacking the genetic alteration to form a blocking duplex (where the reference polynucleotide is a non-target polynucleotide), thereby selective blocking amplification of the reference polynucleotide and enriching amplification of the target polynucleotide.

The disclosed methods and kits may be utilized for diagnosing, prognosing, and treating a subject in need thereof, such as a subject having or suspected of having a disease or disorder. In particular, the disclosed methods and kits may be utilized for diagnosing, prognosing, and treating a subject having cancer or suspected of having cancer. Suitable subjects for the disclosed methods may include cancer patients that currently are in remission.

DETAILED DESCRIPTION

Figure 1:
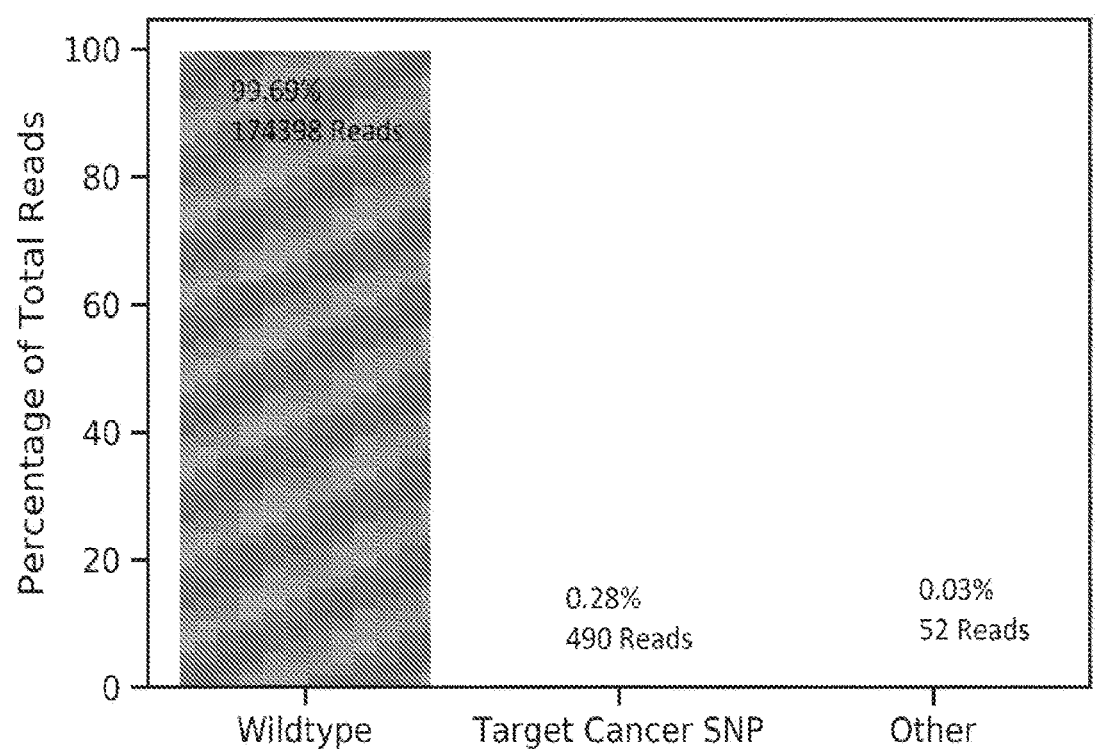
FIG. 1. A mixed sample comprising <0.25% KRAS G12C DNA and >99.75% KRAS wild-type DNA was amplified without the presence of a blocking oligonucleotide and sequenced. 174398 reads were determined to contain the wild-type nucleotide (99.69%), 490 reads contained the KRAS G12C nucleotide (0.28%), and 52 reads contain neither the wild-type or KRAS G12C nucleotide (0.03%).

The present invention is described herein using several definitions, as set forth below and throughout the application.

Unless otherwise specified or indicated by context, the terms "a", "an", and "the" mean "one or more." For example, "a target nucleic acid" should be interpreted to mean "one or more target nucleic acids."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." For example, "a method that includes a step" should be interpreted to mean "a method that comprises a step." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and permitting the inclusion only of additional components that do not fundamentally alter the nature of the claimed subject matter.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the term "subject," which may be used interchangeably with the terms "patient" or "individual," refers to one who receives medical care, attention or treatment and may encompass a human subject. As used herein, the term "subject" is meant to encompass a person having and/or at risk for developing a disease or disorder characterized by a nucleic acid alteration in one or more genetic loci that are associated with the disease or disorder, such as a mutation in a gene that is associated with the disease or disorder. The term "subject" is meant to encompass a person having and/or at risk for developing a cell proliferative disease or disorder such as cancer. The term "subject" is meant to encompass a person having been diagnosed with cancer and currently diagnosed as being in remission. that results in methylation status of one or more genes associated with the disease or disorder or characterized by genetic mutations associated with the disease or disorder. The "methylation status" of a gene may include the "methylation status" of the promoter of the gene, for example, relative to a control gene.

As used herein, a subject in need thereof may include a subject having or at risk for developing a disease or disorder including, but not limited to, a cell proliferative disease or disorder (e.g., cancers such as breast cancer, prostate cancer, colon cancer, lung cancer, gall bladder cancer, brain cancer, uterine cancer, ovarian cancer, head and neck cancer, gastric cancer, liver cancer, leukemias, and lymphomas), a neurodegenerative disease or disorder (e.g., Alzheimer's disease, Parkinson's disease, and Huntington's disease), a psychiatric disease or disorder (e.g., schizophrenia and depression), a metabolic disease or disorder (e.g., type 1 or type 2 diabetes), a cardiovascular disease or disorder (e.g, myocardial infarction or stroke), inflammatory diseases or disorders (e.g. arthritis), and immune diseases or disorders. In some embodiments, the subject has been diagnosed with a cancer and currently is diagnosed as being in remission.

The disclosed methods may be utilized to diagnose or prognose a subject in need thereof based on detecting an alteration in one or more genetic loci associated with the disease or disorder in a sample obtained from the subject. As used herein the terms "diagnose" or "diagnosis" or "diagnosing" refer to distinguishing or identifying a disease, syndrome or condition or distinguishing or identifying a subject having or at risk for developing a particular disease, syndrome or condition. As used herein the terms "prognose" or "prognosis" or "prognosing" refer to predicting an outcome of a disease, syndrome, condition, or treatment regimen in a subject.

The disclosed methods may be utilized to treat a subject in need thereof. For example, the disclosed methods may be utilized to diagnose or prognose a subject in need thereof based on methylation status of the promoter region of one or more genes associated with the disease or disorder or characterized by one or more mutations associated with the disease or disorder. Subsequently to the diagnosis or prognosis, the subject may be administered a suitable treatment based on the diagnosis or prognosis of the disease or disorder.

The disclosed methods may be utilized to characterized nucleic acid in a subject sample. The term "sample" or "subject sample" is meant to include biological samples such as tissues (e.g., tissues obtained from biopsies) and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The methods disclosed herein may be applied when performing DNA amplification of a nucleotide sample. In particular, the methods disclosed herein may be applied when performing DNA amplification of a sample comprising a mixture of a target polynucleotide comprising a genetic alteration and a reference polynucleotide lacking the genetic alteration (where the reference polynucleotide is a non-target polynucleotide). Samples that are analyzed in the disclosed amplification methods may include a mixture comprising a target polynucleotide having one or more genetic alterations at one or more positions as compared to a wild-type polynucleotide (i.e., a mutant polynucleotide) and the wild-type polynucleotide (where the wild-type polynucleotide is a non-target polynucleotide).

The methods disclosed herein may be applied when performing DNA sequence analysis of a nucleotide sample. In particular, the methods disclosed herein may be applied when performing DNA sequence analysis of a sample comprising a mixture of a target polynucleotide comprising a genetic alteration and a reference polynucleotide lacking the genetic alteration (where the reference polynucleotide is a non-target polynucleotide). Samples that are analyzed in the disclosed amplification methods may include a mixture comprising a target polynucleotide having one or more genetic alterations at one or more positions as compared to a wild-type polynucleotide (i.e., a mutant polynucleotide) and the wild-type polynucleotide (where the wild-type polynucleotide is a non-target polynucleotide).

The methods disclosed herein may be applied when performing methylation analysis. For example, the methods disclosed herein may be applied when amplifying and sequencing a polynucleotide sample after the sample has been treated with an agent that selectively modifies unmethylated cytosine residues and not methylated cytosine residues, such as a bisulfite agent. Bisulfite treatment commonly is performed to convert unmethylated cytosine residues to uracil residues in a polynucleotide sample. The treated polynucleotide sample then can be utilized as a template for DNA synthesis (e.g., in a PCR amplification or in a sequencing reaction) where uracil residues ultimately are converted to thymidine residues. By performing sequencing of the treated polynucleotide sample, detection of a thymidine residue at a given position versus a cytosine residue will be indicative of an unmethylated cytosine in the original sample or a methylated cytosine in the original sample, respectively. As such, samples that are analyzed in the disclosed amplification methods may include a mixture comprising a target polynucleotide having a C or T/U at one or more positions as compared to a non-target polynucleotide having a T/U or C at one or more respective positions.

The methods disclosed herein may be applied to a wide variety of sequencing methods. Sequencing methods may include high-throughput or ultra-high-throughput sequencing methods. DNA sequencing processes suitable or adaptable for the disclosed methods may include, but are not limited to, sequencing by synthesis, single-molecule real-time sequencing, ion semiconductor sequencing, pyrosequencing, sequencing by ligation, chain termination sequencing, massively parallel signature sequencing, Polony sequencing, DNA nanoball sequencing, Heliscope single molecule sequencing, Nanopore DNA sequencing, sequencing by hybridization, sequencing with mass spectrometry, microfluidic Sanger sequencing, and microscopy-based sequencing techniques. As such, the disclosed methods may be applied to tradition DNA sequencing methods based on the Sanger sequencing method or the Maxam and Gilbert sequencing method, so-called "first-generation" DNA sequencing techniques, as well as methods that are more amenable to high-throughput analysis, so-called "second generation" and "third generation" DNA sequencing techniques." (See, e.g., Mardis, Ann. Rev. Genomics and Human Genetics, Vol. 9: 387-402 (2008); Metzker, Genome Research, (2005) 15: 1767-1776; Moorthie et al., Hugo J. v. 5 (1-4), December (2011); and Schadt et al., Human Molecular, Genetics, Vol. 19, No. R2, pp. R227-2490 Sep. 21, 2010; and Shendure et al., Nature Biotechnology 26, 1135-1145 (2008).

The disclosed technology relates to nucleic acid and the use of nucleic acid for diagnosing, prognosing, and/or treating diseases and disorders. The terms "nucleic acid" and "oligonucleotide," and "polynucleotide" as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides utilized in the disclosed methods may include one or more modified nucleotides. Nucleotide modifications may include, but are not limited to, locked nucleic acids (LNAs) or bridged nucleic acids (BNAs), peptide nucleic acids, glycol nucleic acids, and threose nucleic acids.

As used herein, a "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full-length polynucleotide. A "variant," "mutant," or "derivative" of a reference polynucleotide sequence may include a fragment of the reference polynucleotide sequence.

A fragment of a target polynucleotide and/or a non-target polynucleotide (i.e., a reference polynucleotide) may be generated via a PCR amplification reaction. An amplification product may comprise amplified fragments of a target polynucleotide and/or a non-target polynucleotide (i.e., a reference polynucleotide). An amplification product may comprise a mixture of amplified fragments of a target polynucleotide and/or a non-target polynucleotide (i.e., a reference polynucleotide).

Regarding polynucleotide sequences, "alteration," "variant," "mutant," or "derivative" may be defined as a nucleic acid sequence having a different nucleic acid sequence relative to a reference sequence, which may include a wild-type sequence. An "alteration," "variant," "mutant," or "derivative" may include a substitution of one or more nucleotides (e.g., a G→t transversion), a deletion of one or more nucleotides, and/or an insertion of one or more nucleotides.

A target polynucleotide may comprise an alteration relative to a reference sequence, which is a non-target polynucleotide. For example, a target polynucleotide may comprise a mutation relative to a wild-type reference sequence. In the disclosed methods, the target polynucleotide selectively is amplified and detected relative to non-target polynucleotide, which may be a wild-type reference polynucleotide.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated. In some embodiments, the samples utilized in the disclosed methods may comprise a nucleic acid sample that has been substantially isolated or purified.

The disclosed methods may utilize a sample comprising nucleic acid from any source, including a source from an animal and/or a source from the environment. In some embodiments, the polynucleotide sample comprises genomic DNA. In further embodiments, the genomic DNA is treated prior to sequencing with a reagent that selectively modifies non-methylated cytosine residues in the DNA to produce detectable modified residues but which does not modify methylated cytosine residues. In even further embodiments, the nucleotide at the nucleotide position of the polynucleotide sample is a methylated cytosine or a modified residue and the set of polynucleotide fragments comprises two or more different polynucleotide fragments having a cytosine or a thymine at the nucleotide position of the polynucleotide sample.

The disclosed methods may utilize primers that are complementary to a target polynucleotide and/or a non-target polynucleotide (i.e., a reference polynucleotide). The disclosed methods also may utilize a blocking oligonucleotide that is complementary to a non-target polynucleotide and which is not complementary to a target polynucleotide at one or more nucleotide positions. As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26 (3/4): 227-259; and Owczarzy et al., 2008, Biochemistry, 47: 5336-5353, which are incorporated herein by reference). Those skilled in the art of nucleic acid technology can determine melting temperature for duplexes.

Methods for Detecting a Target Polynucleotide in a Mixed Sample

The disclosed subject matter relates to methods for detecting a target polynucleotide comprising a genetic alteration relative to a reference polynucleotide lacking the genetic alteration in a sample comprising a mixture of the target polynucleotide and the reference polynucleotide, for example, where the reference polynucleotide is a non-target polynucleotide in the sample. The methods may be utilized for detecting with high sensitivity and high selectivity the target polynucleotide in the mixture of the reference polynucleotide and the target polynucleotide in which the target polynucleotide is present at a low copy number (e.g., less than about 10 copies) and the target polynucleotide represents a low percentage of the mixture of the target polynucleotide and the reference polynucleotide (e.g., less than about 0.125%). The methods may be adapted for diagnosing, prognosing, and treating subjects having a disease or disorder associated with the detected genetic alteration.

The disclosed methods typically include an amplification step that produces an amplification product, such as a polymerase chain reaction (PCR) amplification. The PCR amplification typically is configured to selectively amplify a genetic alteration present in a target polynucleotide relative to a reference polynucleotide lacking the genetic alteration, where the reference polynucleotide is a non-target polynucleotide. The disclosed methods also typically include a sequencing step in which the amplification product is sequenced and the genetic alteration of the target polynucleotide is identified.

In some embodiments, the disclosed methods comprise: (a) performing a polymerase chain reaction (PCR) amplification in a reaction mixture to obtain an amplification product, the reaction mixture comprising: (i) the sample or a fraction of the sample; (ii) a DNA polymerase that lacks 5'→3' nuclease activity and that comprises proofreading activity such as 3'→5' nuclease activity, preferably where the DNA polymerase is a high fidelity polymerase (e.g., a polymerase having an error rate of less than about $10^{-6}$); (ii) a pair of primers that flank the genetic alteration; and (iii) a blocking oligonucleotide that hybridizes selectively to the reference polynucleotide lacking the genetic alteration to form a blocking duplex and obtaining an amplified fragment sample; and (b) sequencing the amplification product and detecting the genetic alteration in the amplification product, thereby detecting the target polynucleotide comprising the genetic alteration in the sample. The reaction mixture further may comprise additional components for performing a PCR amplification (e.g., buffer, NTP's, divalent cation, and the like).

The disclosed methods may be performed in order to detect a target polynucleotide that represents no more than about 3%, 2%, 1%, 0.5%, 0.25%, 0.125%, or less of the mixture of the target polynucleotide and the reference polynucleotide in the sample. In some embodiments of the disclosed methods, the target polynucleotide represents no more than about 0.125% of the mixture of the target polynucleotide and the reference polynucleotide in the sample.

The disclosed methods may utilize a polymerase that has a relatively low error rate. In some embodiments, the polymerase has an error rate which is less than about $10^{-5}$, $10^{-6}$, or $10^{-7}$.

The disclosed methods typically include an amplification step comprising a number of amplification cycles. In some embodiments of the disclosed methods, the methods include a PCR amplification step in which PCR amplification is performed for no more than 60, 50, 40, or 30 cycles.

In the disclosed methods, the genetic alteration of the target nucleotide is selectively amplified or enriched. In some embodiments of the disclosed methods, the genetic alteration is detected in at least about 90%, 95%, 96%, 97%, 98%, or 99% of the sequenced amplified product. In some embodiments of the disclosed methods, the amplification product is sequenced from multiple reads and the genetic alteration is detected in at least about 90%, 95%, 96%, 97%, 98%, or 99% of the multiple reads.

In the disclosed methods, the genetic alteration of the target polynucleotide is selectively enriched and detected. In some embodiments of the disclosed methods, the target polynucleotide comprising the generic alteration represents no more than about 0.125% of the mixture of the target polynucleotide and the reference polynucleotide lacking the genetic alteration in the sample. After the disclosed methods have been performed, in some embodiments the amplification product is sequenced from multiple reads and the genetic alteration is detected in at least about 90%, 95%, 96%, 97%, 98%, or 99% of the multiple reads, representing an enrichment of at least about 720 fold (i.e., 90%/0.125%=720).

The disclosed methods typically include sequencing an amplification product. In some embodiments of the disclosed methods, the blocking oligonucleotide is removed from the amplification product prior to sequencing the amplification product.

The disclosed methods typically detect a target nucleotide that present in a mixed sample comprising the target nucleotide and a reference polynucleotide. In some embodiments, the disclosed methods include a step of determining the minimum number of PCR cycles necessary for detecting the target polynucleotide when the target polynucleotide is present in the mixture at a relative low percentage (e.g., when the target polynucleotide is present in the mixture at a percentage of no more than 0.1%, 0.05%, 0.02%, or 0.01%).

In the disclosed methods, the target polynucleotide may be present at a relative low concentration in the sample. In some embodiments, the target nucleotide may be present in a sample at a copy number of less than about 10000, 1000, 100, 10 or less. In some embodiments, the disclosed methods include a step of determining the minimum number of PCR cycles necessary for detecting the target polynucleotide when the target polynucleotide is present in the sample at a copy number of less than about 10000, 1000, 100, 10 or less.

In the disclosed methods, the genetic alteration of the target nucleotide is selectively amplified or enriched. The genetic alteration may be selectively amplified or enriched by configuring the PCR amplification reaction to include a blocking oligonucleotide that selectively hybridizes to the reference polynucleotide to form a blocking duplex, where the reference polynucleotide lacks the generic alteration and the reference polynucleotide is a non-target polynucleotide. In some embodiments, the blocking oligonucleotide comprises one or more modified nucleotides that enhance the stability of the duplex formed by the blocking oligonucleotide and the reference polynucleotide. In some embodiments the blocking oligonucleotide comprises one or more modified nucleotides that enhance the selectivity of the blocking oligonucleotide for hybridizing to the reference polynucleotide relative to the target polynucleotide.

The blocking oligonucleotide may form a first duplex with the reference polynucleotide lacking the genetic alteration (i.e., where the reference polynucleotide is a non-target polynucleotide), where the first duplex has a first melting temperature T1. The blocking oligonucleotide may form a second duplex with the target polynucleotide comprising the genetic alteration, where the second duplex has a first melting temperature T2. Preferably T1>T2. In some embodiments, the blocking oligonucleotide is configured such that T1 is at least about 1, 2, 3, 4, 5, 6, 7, 8, 9, 10, 11, 12, 13, 14, or 15° C. higher than T2 (i.e., T1−T2>than about 1, 2, 3, 4, 5, 6, 7, 8, 9, 10, 11, 12, 13, 14, or 15° C.).

In the disclosed methods, the blocking oligonucleotide may comprise or consist of modified nucleotides. Modified nucleotides may include but are not limited to locked nucleic acids (LNAs) or bridge nucleic acids (BNAs), peptide nucleic acids, glycol nucleic acids, and threose nucleic acids. The presence of modified nucleotides in the blocking oligonucleotide may alter T1 or T2. Preferably, the presence of modified nucleotides in the blocking oligonucleotide increases T1. Preferably, the presence of modified nucleotides in the blocking oligonucleotide increases the difference between T1 and T2.

In the disclosed methods, the temperature of the PCR reaction mixture may be increased to melt the target polynucleotide and reference polynucleotide in order to form single-stranded DNA. The temperature then may be lowered to the point where the blocking oligonucleotide hybridizes to the reference polynucleotide selectively because the blocking oligonucleotide is configured to have a lower melting temperature when hybridized to the target polynucleotide. As such, a higher percentage of reference polynucleotides will be hybridized with the blocking oligonucleotide as compared to the percentage of target polynucleotides Primer oligonucleotides which flank the position where the blocking oligonucleotide hybridizes then are used to amplify the target oligonucleotide and the reference oligonucleotide. During the PCR amplification, the hybridization of the blocking oligonucleotide to the reference polynucleotide inhibits the extension of the polymerase. As a result, if a target polynucleotide is present, the target polynucleotide will be amplified to a higher extent as compared to the reference polynucleotide. As a consequence, after each PCR cycle the amplification product of the target polynucleotide is enriched. Multiple PCR cycles may be performed to increase the total number of copies of the amplification product of the target polynucleotide to a point where sequencing may be performed in order to detect the genetic alteration of the target polynucleotide.

Preferentially in the disclosed methods, extension during amplification is performed at a temperature at which the blocking oligonucleotide is hybridized to a relatively high percentage of the reference polynucleotide (which is a non-target polynucleotide) in the sample, such as a temperature at which the blocking oligonucleotide is hybridized to greater than about 50%, 60%, 70%, 80%, 90%, 95%, or greater of the reference polynucleotide (which is a non-target polynucleotide) in the sample. Preferably in the disclosed methods, extension during amplification is performed at a temperature at which the blocking oligonucleotide is hybridized to a relatively low percentage of the target polynucleotide in the sample, such as a temperature at which the blocking oligonucleotide is hybridized to less than about 50%, 40%, 30%, 30%, or lower of the target polynucleotide in the sample.

The blocking oligonucleotides may include locked nucleic acid (LNA) also known as bridged nucleic acid (BNA). An LNA is a modified nucleotide in which the sugar moiety (e.g., ribose) is modified with a bridge connecting the 2' oxygen and 4' carbon (i.e., where the 2'-O and 4'-C are conjugated via a bridging moiety). The bridge "locks" the sugar moiety in the 3'-endo (North) conformation, which is often found in A-form duplexes. This structure provides for increased stability against enzymatic degradation, and also offers improved specificity and affinity in base-pairing as a constituent of an oligonucleotide. LNA nucleotides can be mixed with DNA or RNA residues in an oligonucleotide. Bridging moieties of LNA may include alkylene moieties (e.g., a methylene bridging moiety) and amino alkylene moieties (e.g., amino methylene bridging moiety). An LNA may be referred to with the following designation: +A, +G, +C, or +T. In some embodiments of the blocking oligonucleotides, all of the nucleotides of the blocking oligonucleotide are LNAs.

The disclosed methods may utilize a blocking oligonucleotide that is relatively short in length. In some embodiments, the blocking oligonucleotide has a length that is no more than about 20, 19, 18, 17, 16, 15, 14, 13, 12, 11, or 10 nucleotides.

The disclosed methods may be performed to detect a target polynucleotide comprising a genetic alteration relative to a reference polynucleotide, where the reference polynucleotide is a non-target polynucleotide. The genetic alteration may include a mutation relative to a wild-type sequence, for example, where the target polynucleotide comprises the mutation and the reference polynucleotide comprises the wild-type sequence and the reference polynucleotide is a non-target wild-type polynucleotide. Genetic alterations that are detected in the disclosed methods may include substitutions, deletions, insertions, or a combination thereof.

The genetic alterations detected in the disclosed methods may be present at selected genetic loci. In some embodiments, the genetic alteration is present in a genetic loci selected from one or more of PIK3CA, KRAS, APC, FAT4, KMT2D, KMT2C, and BRAF.

In some embodiments of the disclosed methods, the methods utilize a an additional pair of primers that amplify a control sequence as an internal control. An internal control may be utilized to demonstrate that steps of the disclosed methods are occurring as intended and/or if a blocking oligonucleotide is blocking exponential amplification of the reference polynucleotide as intended.

The disclosed methods may be configured in order to detect multiple target polynucleotides comprising different genetic alterations relative to a reference polynucleotide. In some embodiments, the disclosed methods are configured for performing a multiplex analysis.

In some embodiments, the disclosed methods are configured for detecting two or more target polynucleotides each comprising a different genetic alteration relative to a reference polynucleotide lacking the genetic alterations in a sample (where the reference polynucleotide is a non-target polynucleotide in the sample) comprising a mixture of the two or more target polynucleotides and the reference polynucleotide. The disclosed methods may include: (a) performing a polymerase chain reaction (PCR) amplification to obtain an amplification product in a reaction mixture comprising: (i) the sample or a fraction of the sample; (ii) a DNA polymerase that lacks 5'→3' nuclease activity and 3'→5' nuclease activity (e.g., a thermostable polymerase comprising 3'→5' nuclease activity) and preferably the DNA polymerase is a high fidelity polymerase (e.g., a thermostable polymerase having an error rate of less than about $10^{-6}$); (iii) two or more pairs of primers, wherein each pair of primers flank one of the different genetic alterations; and (iv) two or more blocking oligonucleotides, each configured to hybridize selectively to the reference polynucleotide lacking the different genetic alterations to form two or more blocking duplexes; and (b) sequencing the amplification product and detecting the different genetic alterations in the amplification product, thereby detecting the two or more target polynucleotides comprising the different genetic alterations in the sample. The reaction mixture further may comprise additional components for performing a PCR amplification (e.g., buffer, NTP's, divalent cation, and the like).

The disclosed methods may be performed to detect a target polynucleotide in a sample. Suitable samples may include, but are not limited to, biological samples or environmental samples.

In some embodiments, the sample is a blood sample or a blood product sample (e.g., plasma or serum). In some embodiments, the sample is a cell-free sample, such as a cell-free blood sample, for example, wherein the blood sample has been treated to remove cells prior to performing the disclosed methods.

The disclosed methods may be performed in order to detect a genetic alteration in a target polynucleotide relative to a reference polynucleotide. In some embodiments, the disclosed methods may be performed in order to detect methylation in a target polynucleotide relative to a reference polynucleotide. In some embodiments of the disclosed methods, prior to the methods being performed the sample is treated with a reagent that selectively modifies non-methylated cytosine residues to produce detectable modified residues (e.g., uracil residues) but which does not modify methylated cytosine residues, such as a bisulfite reagent. In some methods, the target polynucleotide and the reference polynucleotide may differ based on the presence of a detectable modified residue (e.g., uracil or thymidine) versus a methylated cytosine residue.

The disclosed methods may be performed in order to detect a genetic alteration in a target polynucleotide relative to a reference polynucleotide. In some embodiments, the genetic alteration is associated with cancer in a subject, such as a mutation associated with cancer in a subject. In some embodiments, prior to performing the initial step of the disclosed methods, the methods comprise sequencing a cancer sample from the subject and detecting the genetic alteration in the cancer sample and determining that the cancer is associated with the genetic alteration. The disclosed methods then may be performed in order to monitor the presence of the genetic alteration in the subject, where the presence of the genetic alteration indicates the progression of cancer in the subject.

In some embodiments of the disclosed methods, the sample is obtained from a subject that has cancer or is at risk for developing cancer. In some embodiments of the disclosed methods, the subject has been diagnosed with cancer and currently is in remission, for example, after the subject has been treated for the diagnosed cancer. The disclosed methods may be performed in order to monitor for cancer recurrence in a subject, where detection of the genetic alteration in the subject indicates that the cancer has recurred.

Also disclosed herein are kits for performing the disclosed methods. The disclosed kits may comprise one or more components for performing the disclosed methods. In some embodiments, the kits comprise one or more of: (i) a DNA polymerase that lacks 5'→3' nuclease activity and comprises 3'→5' nuclease activity and preferably wherein the DNA polymerase is a high fidelity polymerase (e.g., a thermostable polymerase having an error rate which is less than about $10^{-6}$), (ii) one or more pairs of primers that flank the genetic alteration, and/or (iii) one or more blocking oligonucleotides that hybridize selectively to the reference polynucleotide lacking the genetic alteration to form a blocking duplex. In some embodiments, the kits comprise one or more of: (i) a DNA polymerase that lacks 5'→3' nuclease activity and comprises 3'→5' nuclease activity; (ii) one or more pairs of primers that flank a genetic alteration in a genetic loci selected from PIK3CA, KRAS, APC, FAT4, KMT2D, KMT2C, and BRAF; and/or (iii) one or more blocking oligonucleotides that hybridize selectively to the reference polynucleotide lacking the genetic alteration to form a blocking duplex and obtaining an amplified fragment sample (i.e., a blocking oligonucleotide that hybridizes to one or more more of wild-type PIK3CA, KRAS. APC, FAT4, KMT2D, KMT2C, and BRAF at the position of the corresponding genetic alteration). The disclosed kits may comprise a blocking oligonucleotide that consists of LNAs and the blocking oligonucleotide may be no longer than 20, 19, 18, 17, 16, 15, 14, 13, 12, 11, or 10 nucleotides.

The disclosed methods and kits may be utilized for diagnosing, prognosing, and treating a subject in need thereof, such as a subject having or suspected of having a disease or disorder. The disclosed methods may include diagnosing and/or prognosing a subject in need thereof and further may include subsequently administering treatment to the subject in need thereof after diagnosing and/or prognosing the subject. The methods contemplated herein may include: (a) requesting an analysis that detects a target polynucleotide comprising a genetic alteration; and (2) subsequently administering a treatment to a subject based on the results of the analysis.

EXAMPLES

The following Examples are illustrative and should not be interpreted to limit the scope of the claimed subject matter.

Example 1

This example describes how a low frequency variant was enriched and detected. In this example the low frequency variant is the KRAS G12C mutation, known to be associated with or present in some cancers.

DNA for KRAS wild-type (catalog HD710) and KRAS G12C (catalog HD269) were purchased from Horizon Discovery. Oligonucleotides, including the primers and the blocker, were purchased from Integrated DNA Technologies. Q5 High-Fidelity 2× Master Mix (catalog M0492S) and Monarch PCR and DNA cleanup kit (T1030S) were purchased from New England Biolabs.

The KRAS wild-type sequence is provided by SEQ ID NO:1:

```
                                         (SEQ ID NO: 1)
CTTATGTGTGACATGTTCTAATATAGTCACATTTTCATTATTTTTATTAT

AAGGCCTGCTGAAAATGACTGAATATAAACTTGTGGTAGTTGGAGCTGGT

GGCGTAGGCAAGAGTGCCTTGACGATACAGCTAATTCAGAATC
```

The KRAS G12C sequence is provided by SEQ ID NO:2 and includes a G→t transversion:

```
                                         (SEQ ID NO: 2)
CTTATGTGTGACATGTTCTAATATAGTCACATTTTCATTATTTTTATTAT

AAGGCCTGCTGAAAATGACTGAATATAAACTTGTGGTAGTTGGAGCTtGT

GGCGTAGGCAAGAGTGCCTTGACGATACAGCTAATTCAGAATC
```

Primers were designed as follows:

```
Forward Primer (SEQ ID NO: 3): CTTATGTGTGACATGTTC

Reverse Primer (SEQ ID NO: 4) GATTCTGAATTAGCTGTA
TC
```

The oligonucleotide blocker consisted of LNAs (designated as +A, +G, +C, or +T) as follows:
Oligonucleotide Blocker (SEQ ID NO:5) +A+G+C+T+G+G+T+G+G+C The total reaction volume of 100 µl was prepared as follows:
Forward primer: 0.1 µM working concentration (1 µl of 10 µM stock)
Reverse primer: 0.1 µM working concentration (1 µl of 10 µM stock)
Wild-type: 50 ng (14500 copies) (1 µl of 50 ng/µl)
Heterozygous KRAS G12C: 0.25 ng (36 copies, 18 copies of mutant and 18 wild-type) (0.5 µl of 0.5 ng/µl)
Blocker: 0.2 µM (working concentration (1 µl of 20 µM stock)
2×Q5 Master Mix: 1× working concentration (50 uµl of 2× Master Mix)
Water (45.5 µl)

The forward primer (SEQ ID NO:3) and the reverse primer (SEQ ID NO:4) were at a final concentration of 0.1 µM. The blocker (SEQ ID NO:5) was at a concentration of 0.2 µM. Q5 High-Fidelity 2× Master Mix was at a 1× concentration. 50 ng KRAS wild-type DNA was added and 0.25 ng of KRAS G12C DNA was added to create a mixture. The KRAS G12C DNA was heterozygous so that DNA having the KRAS G12C mutation represented <0.25% of the mixture (i.e., 0.25 ng/2=0.125 ng KRAS G12C DNA/(50 ng+0.25 ng)<0.25%). The amount of KRAS wild-type NA contained 14500 copies, whereas the amount of KRAS G12C DNA contained 36 copies, 18 of which were mutant DNA and 18 of which were wild-type DNA due to the heterozygosity of the KRAS G12C DNA. The working solution was briefly vortexed, and 25 µl was aliquoted into thin-walled PCR tubes. As such each tube contained 9 copies of KRAS G12C mutant DNA.

A PCR protocol was performed as follows: 95° C. for 60 seconds, 55 cycles of (95° C. for 10 seconds, 70° C. for 5 seconds, and 55° C. for 25 seconds), 70° C. for 60 seconds.

The PCR product was purified using the Monarch PCR cleanup protocol. The purified product was diluted to 20 ng/ul and sequenced using Azenta Genewiz Amplicon EZ service.

Raw sequence reads were aligned to the mutant and wild-type sequence. Reads were separated into 3 categories (wild-type nucleotide (G), KRAS G12C nucleotide (t), or other nucleotide) present with or without additional mutations in the read outside of the KRAS G12C mutation. The starting mixture had <0.25% mutant KRAS G12C DNA. After the enrichment, the reads containing the KRAS G12C mutations represented greater than 95% of the quality reads.

FIG. 1 illustrates the results of a control reaction. The mixed sample comprising <0.25% KRAS G12C DNA and >99.75% KRAS wild-type DNA was amplified without the presence of a blocking oligonucleotide and sequenced. 174398 reads were determined to contain the wild-type nucleotide (99.69%), 490 reads contained the KRAS G12C nucleotide (0.28%), and 52 reads contain neither the wild-type or KRAS G12C nucleotide (0.03%).

Figure 2:
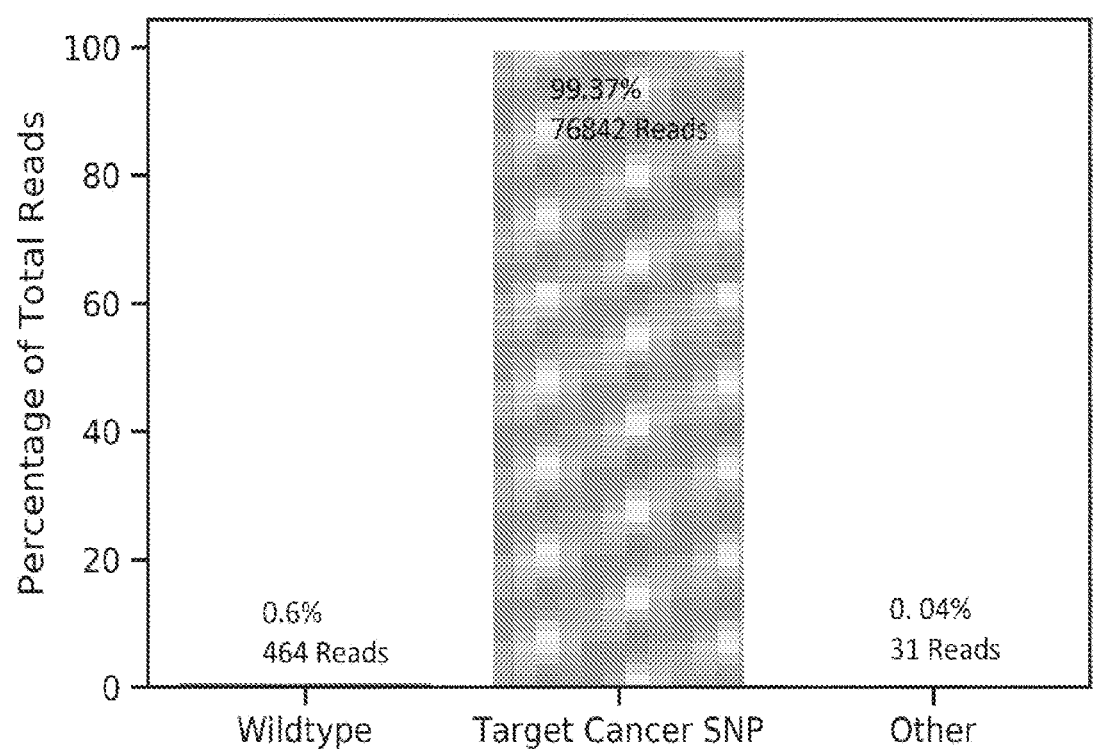
FIG. 2. A mixed sample comprising <0.25% KRAS G12C DNA and >99.75% KRAS wild-type DNA was amplified in the presence of a blocking oligonucleotide and sequenced. 464 reads were determined to contain the wild-type nucleotide (0.6%), 76842 reads contained the KRAS G12C nucleotide (99.37%), and 31 reads contain neither the wild-type or KRAS G12C nucleotide (0.04%). These results indicate that the presence of the LNA blocker enriched the sample about 354 times and increased the raw reads about 157 times.

FIG. 2 illustrates the results of the test reaction with a blocking oligonucleotide. The mixed sample comprising <0.25% KRAS G12C DNA and >99.75% KRAS wild-type DNA was amplified in the presence of a blocking oligonucleotide (SEQ ID NO:5) and sequenced. 464 reads were determined to contain the wild-type nucleotide (0.6%), 76842 reads contained the KRAS G12C nucleotide (99.37%), and 31 reads contain neither the wild-type or KRAS G12C nucleotide (0.04%).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. A method for enriching a double-stranded target polynucleotide in a sample to obtain an amplification product, the method comprising the steps of:
   (a) preparing a reaction mixture comprising:
      (i) the sample, wherein the sample comprises a double-stranded reference polynucleotide and the double-stranded target polynucleotide, wherein the target polynucleotide comprises a genetic alteration and the reference polynucleotide lacks the genetic alteration, wherein the genetic alteration is a substitution of one or more nucleotides, a deletion of one or more nucleotides, and/or an insertion of one or more nucleotides;
      (ii) a DNA polymerase that lacks 5'→3' nuclease activity and comprises 3'→5' nuclease activity;
      (iii) a blocking oligonucleotide that has a length of 8-20 nucleotides, consists of locked nucleic acids (LNAs) comprising a sugar moiety having a 2'-O conjugated to 4'-C via a methylene group, and is complementary to the reference polynucleotide and not complementary to the target polynucleotide;
      (iv) a pair of oligonucleotide primers that flank the genetic alteration,
         wherein a forward primer of the primer pair is capable of hybridizing to a first strand of the double-stranded reference polynucleotide and to a first strand of the double-stranded target polynucleotide, and
         wherein a reverse primer of the primer pair is capable of hybridizing to a second strand of the double-stranded reference polynucleotide and to a second strand of the double-stranded target polynucleotide,
         wherein the forward and reverse primers of the primer pair flank the genetic alteration in the target polynucleotide, and
         wherein the forward and reverse primers of the primer pair do not overlap with the sequence complementary to the blocking oligonucleotide;
   (b) heating the reaction mixture above a temperature to melt the double stranded reference polynucleotide and the double stranded target polynucleotide;

(c) cooling the reaction mixture to a temperature wherein the blocking oligonucleotide hybridizes to the reference polynucleotide to form a blocking duplex,
  but wherein the blocking oligonucleotide does not hybridize to the target polynucleotide, and wherein the forward and reverse primers of the primer pair do not hybridize to the reference polynucleotide or to the target polynucleotide;
(d) cooling the reaction mixture, wherein the forward primer hybridizes to the reference polynucleotide and the reverse primer hybridizes with the reference polynucleotide, and wherein the forward primer hybridizes with the target polynucleotide and the reverse primer hybridizes with the target polynucleotide;
(e) extending the primers hybridized to the target polynucleotide or to the reference polynucleotide; and
(f) repeating steps (b) through (e) for two or more cycles to form the amplification product containing target polynucleotides, thereby enriching the quantity of target polynucleotides relative to the reference polynucleotides in the amplification product as compared to the sample.

2. The method of claim 1, wherein the DNA polymerase has an error rate of less than $10^{-5}$.

3. The method of claim 1, wherein the blocking oligonucleotide comprises one or more modified nucleotides that enhance the selectivity of the blocking oligonucleotide for hybridizing to the reference polynucleotide relative to the target polynucleotide.

4. The method of claim 1, wherein a DNA binding fluorophore is added to the mixture.

5. The method of claim 1, wherein an oligonucleotide probe is added to the mixture.

6. The method of claim 1, further comprising
  (g) sequencing amplification product containing target polynucleotides.

7. A method for enriching a double-stranded target polynucleotide in a sample to obtain an amplification product, the method consisting of the steps of:
  (a) preparing a reaction mixture comprising:
    (i) the sample, wherein the sample comprises a double-stranded reference polynucleotide and the double-stranded target polynucleotide, wherein the target polynucleotide comprises a genetic alteration and the reference polynucleotide lacks the genetic alteration, wherein the genetic alteration is a substitution of one or more nucleotides, a deletion of one or more nucleotides, and/or an insertion of one or more nucleotides;
    (ii) a DNA polymerase that lacks 5'→3' nuclease activity and comprises 3'→5' nuclease activity;
    (iii) a blocking oligonucleotide that has a length of 8-20 nucleotides, consists of locked nucleic acids (LNAs) comprising a sugar moiety having a 2'-O conjugated to 4'-C via a methylene group, and is complementary to the reference polynucleotide and not complementary to the target polynucleotide;
    (iv) a pair of oligonucleotide primers that flank the genetic alteration,
      wherein a forward primer of the primer pair is capable of hybridizing to a first strand of the double-stranded reference polynucleotide and to a first strand of the double-stranded target polynucleotide, and
      wherein a reverse primer of the primer pair is capable of hybridizing to a second strand of the double-stranded reference polynucleotide and to a second strand of the double-stranded target polynucleotide,
      wherein the forward and reverse primers of the primer pair flank the genetic alteration in the target polynucleotide, and
      wherein the forward and reverse primers of the primer pair do not overlap with the sequence complementary to the blocking oligonucleotide;
  (b) heating the reaction mixture above a temperature to melt the double stranded reference polynucleotide and the double stranded target polynucleotide;
  (c) cooling the reaction mixture to a temperature wherein the blocking oligonucleotide hybridizes to the reference polynucleotide to form a blocking duplex,
    but wherein the blocking oligonucleotide does not hybridize to the target polynucleotide, and wherein the forward and reverse primers of the primer pair do not hybridize to the reference polynucleotide or to the target polynucleotide
  (d) cooling the reaction mixture, wherein the forward primer hybridizes to the reference polynucleotide and the reverse primer hybridizes with the reference polynucleotide, and wherein the forward primer hybridizes with the target polynucleotide and the reverse primer hybridizes with the target polynucleotide;
  (e) extending the primers hybridized to the target polynucleotide or to the reference polynucleotide;
  (f) repeating steps (b) through (e) for two or more cycles to form the amplification product containing target polynucleotides, thereby enriching the quantity of target polynucleotides relative to the reference polynucleotides in the amplification product as compared to the sample; and optionally
  (g) sequencing amplification product containing target polynucleotides.

* * * * *